United States Patent [19]
Studer et al.

[11] Patent Number: 6,146,383
[45] Date of Patent: Nov. 14, 2000

[54] PIVOTAL SECURING SYSTEM AT A BONE SCREW

[75] Inventors: Armin Studer; Cosimo Donno, both of Winterthur; Markus Fröhlich, Balterswil, all of Switzerland

[73] Assignee: Sulzer Orthopädie AG, Baar, Switzerland

[21] Appl. No.: 09/241,824

[22] Filed: Feb. 1, 1999

[30] Foreign Application Priority Data

Feb. 2, 1998 [EP] European Pat. Off. ............. 98810076
Sep. 24, 1998 [EP] European Pat. Off. ............. 98810957

[51] Int. Cl.⁷ ........................................... A61B 17/86
[52] U.S. Cl. ........................................ 606/61; 606/73
[58] Field of Search ................. 606/54, 56, 59, 606/60, 61, 69, 70, 71, 72, 73

[56] References Cited

U.S. PATENT DOCUMENTS 5,735,850 4/1998 Baumgartner et al. ................ 606/61
5,752,957 5/1998 Ralph et al. ............................. 606/61

FOREIGN PATENT DOCUMENTS

0504103A1  9/1992  European Pat. Off. .
0614649A1  9/1994  European Pat. Off. .
19542116A1 5/1997  Germany .
WO 96/29947 10/1996 WIPO .

*Primary Examiner*—Michael Buiz
*Assistant Examiner*—David O. Reip
*Attorney, Agent, or Firm*—Townsend and Townsend and Crew LLP

[57] ABSTRACT

With the invention a pivotal securing system between a bone screw (1) with a spherical head part (2) and a reception part (3) is shown. The reception part has a passage bore (4) with a shoulder at its end which encloses the head part (2) at its lower side and which forms an abutment when the head part (2) is pressed on by the clamping screw (7) in a settable pivotal position (8). The head part (2) is executed as a separate part (9) which can be screwed together with the bone screw (1) in order to be able to place on the reception part (3) and to connect it to the latter after the implantation of the bone screw (1).

13 Claims, 5 Drawing Sheets

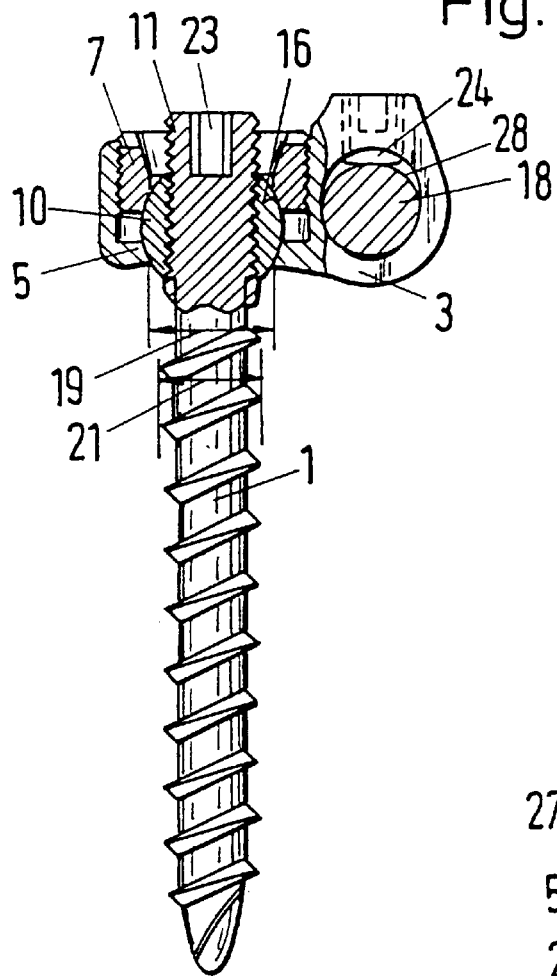
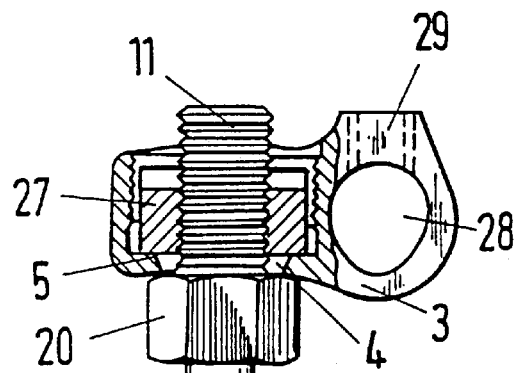
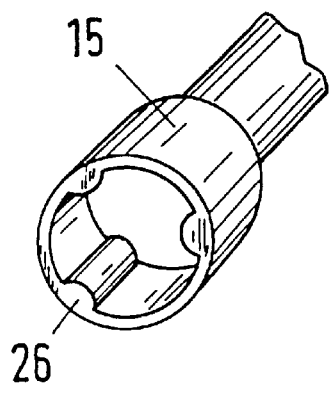
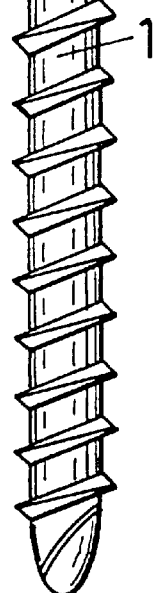

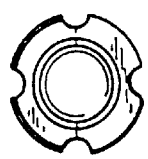
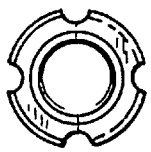
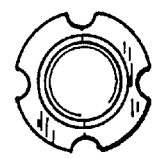
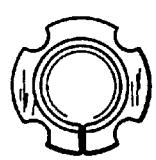

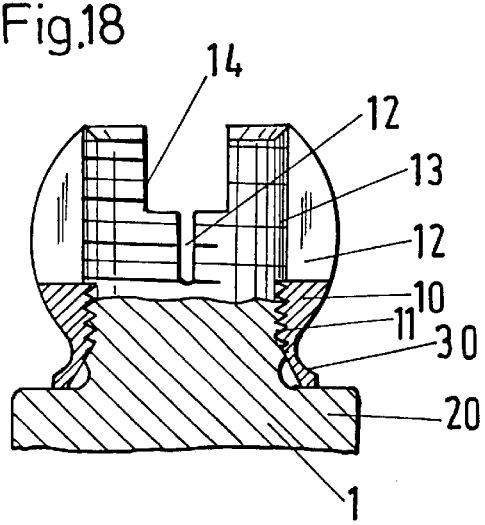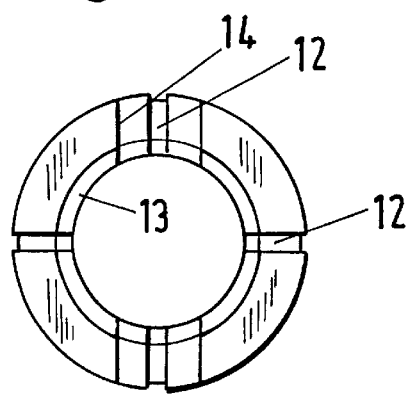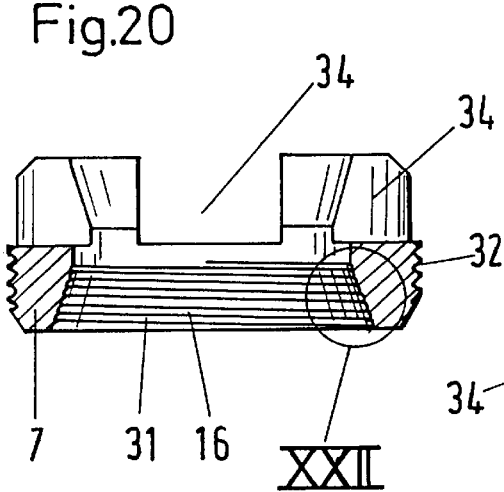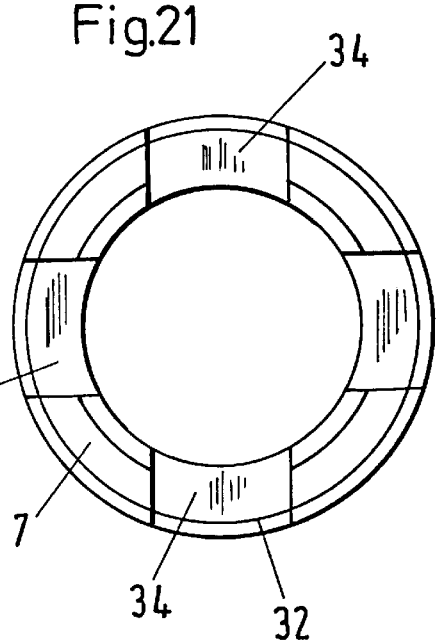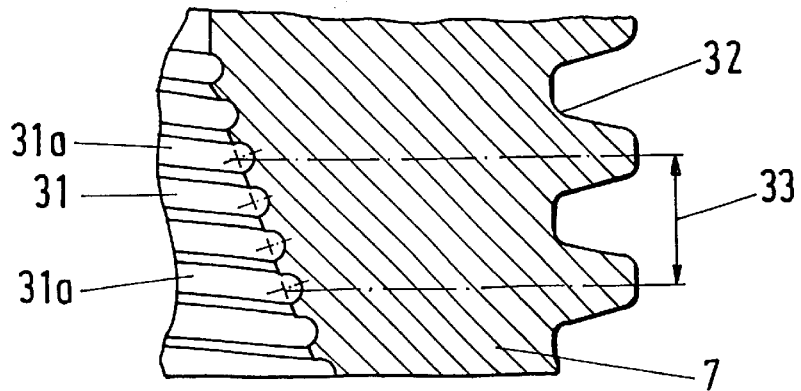

PIVOTAL SECURING SYSTEM AT A BONE SCREW

The invention relates to a pivotal securing system between a bone screw with a spherical head part and a reception part which, at the end of a passage bore, encloses the head part with a shoulder at its lower side and which receives a clamping screw in the passage bore by means of which the head part can be pressed against the shoulder in a selectable pivotal position.

BACKGROUND OF THE INVENTION

A bone screw is shown in EP-A-0 614 649 which must be inserted through a reception part prior to being rotated into an implant, which is a hindrance during the rotating in. Precisely in vertebral corrections a plurality of bone screws of this kind, which are screwed into different vertebrae, are connected to one another via connection rods and reception parts. The reception part is designed in the shape of a tower and receives the spherical head of the bone screw within itself. The bone screw is pivotally journalled at a counter-shell with its spherical head and can be fixed to the reception part either directly by a clamping screw or indirectly by a clamping screw via intermediate members such as connection rod and pressure disc.

Similar considerations are shown in DE-A-195 42 116 for a plate-shaped reception part which is pivotal about the common centre of these spherical surfaces prior to the fixing of spherical surfaces of the screw head.

Common to both arrangements is that the bone screw must be screwed in through the reception part.

SUMMARY OF THE INVENTION

The object of the invention is to remedy this condition. This object is satisfied in that the spherical head part is designed as a separate part which can be screwed together with the bone screw in order to be able to place on the reception part and to connect it to the latter after the implantation of the bone screw.

The arrangement has the advantage that the bone screw, for example as a pedicle screw, is freely accessible during the screwing in. A surgeon can monitor the position and seating of the screw as well as the state of the bone tissue during the screwing in. In the combination of a plurality of pedicle screws the reception parts can be provisorily secured to pre-bent connection rods and corrected in their position by placing on at the pedicle screws in order subsequently to secure the separate spherical heads to the pedicle screws and to screw clamping screws in loosely. The provisorily fixed connection rods can once again be loosened in their securing to the reception part and then all connections can be tightened uniformly. This procedure is recommended if the vertebrae are aligned with respect to one another. If however displacements of the vertebrae are required, a loosening of the reception parts which are aligned on the connection rods is intentionally dispensed with. A further advantage is a construction of the reception part of low height and the possibility of using standard pedicle screws in order to arrive at a reasonable pivotal range and at an easier insertion of the pedicle screws.

The execution of the separate spherical head part as a screw nut which can be screwed together with a screw-like extension of the bone screw extends the field of use of the standard pedicle screws. Since these screw nuts are weakened by slits, they fasten themselves to their counter-threads when being pressed together. The bone screw need therefore not necessarily have an abutment on its screw-like extension for the spherical screw nut. The screw nut can therefore also be adjusted in its height and then fixed to the counter-thread through pressing together. Engagement surfaces in the form of indentations facilitate the height adjustment of the spherical screw nut. The shoulder of the reception part and the pressing surface of the clamping screw are formed as conical surfaces, the half cone angle a of which should lie within certain limits $8°<\alpha<25°$ in order to achieve a good clamping action and a low space requirement. With the conical surfaces against a spherical surface the force application points are practically at the same location and hardly dependent on manufacturing tolerances even in elastic and slightly plastic deformations. The springing in of the screw nut, which is weakened by slits, can be attuned to these constant force application points. In addition to the friction between the conical surfaces and the spherical surface, an elastic and a plastic deformation in the form of a flattening also take place, which causes material to protrude in the region of the indentations of the spherical surface and likewise acts counter to a rotation. This kind of a connection permits bone screws with and without a collar to be used, height adjustments to be carried out at the screw shaped extension of the bone screw and thread diameters to be used at the actual bone screw which are greater than the inner diameter of the shoulder in the reception part.

If the spherical nut has slits only from above and a neck is formed at its lower side which is supported on a shoulder of the bone screw as a closed ring outside the outer diameter of the screw-like extension, the closed ring can be tensioned against the shoulder of the bone screw when the nut is rotated in. This has the advantage that at a specific transmission torque which acts at the spherical nut, lower bending stress peaks arise at the screw-shaped extension of the bone screw.

A further improvement consists in providing the clamping screw at its clamping surface with a thread in the form of a spirally arranged groove, with this groove or, respectively, the threading being in the same direction as the outer thread of the clamping screw and having the same pitch as the outer thread. With a measure of this kind it is ensured that the direction of the spiral groove and its relative movement with respect to the spherical head part coincide during the clamping. The protruding threaded part can deform itself and the spherical surface plastically to a limited extent so that a force-locked and a form-locked connection arises which is particularly suitable for the transmission of bending torques to a spherical head. In principle every spherical head which is captured in a threaded bore and is fixed with a clamping screw with an inwardly lying pressing surface can be improved in the transmission of a maximum bending torque with this measure when the pressing surface has a spiral thread which is directed similarly to the outer thread of the clamping screw and which has the same pitch. Since the depth of the spiral thread need not be large for the clamping, it has proved useful to execute the spiral thread multiply. An improvement of the transmittable torques also arises when the deformations are only in the elastic range.

BRIEF DESCRIPTION OF THE DRAWINGS

In the following the invention will be described with reference to exemplary embodiments. Shown are:

FIG. 5 is schematically, a pedicle screw without a collar with a spherical head part which is adjustable in height and which is formed as a nut;

FIG. 6 is schematically, an arrangement in accordance with FIG. 3 in which, for a mounting which can not be pivoted out of the axis, the clamping screw and the spherical nut were replaced by a differently dimensioned securing nut;

FIG. 16 is schematically, the head of a screwing tool which can be used for the screw nuts of FIGS. 7, 8 and 9.

FIG. 18 is schematically and enlarged in a longitudinal section, a further embodiment of a spherical nut with a neck which is formed on for the support on a shoulder of the bone screw;

FIG. 19 is schematically, the nut of FIG. 18 in a plan view;

FIG. 20 is schematically and enlarged, in a longitudinal section, a further embodiment of a clamping screw;

FIG. 21 is schematically and enlarged, a plan view of the clamping screw of FIG. 20; and FIG. 22 is schematically, a section of the clamping screw of FIG. 20 which is once again enlarged, with an inner thread on the pressing surface for the spherical head part.

DESCRIPTION OF THE PREFERRED EMBODIMENTS

Figure 1:
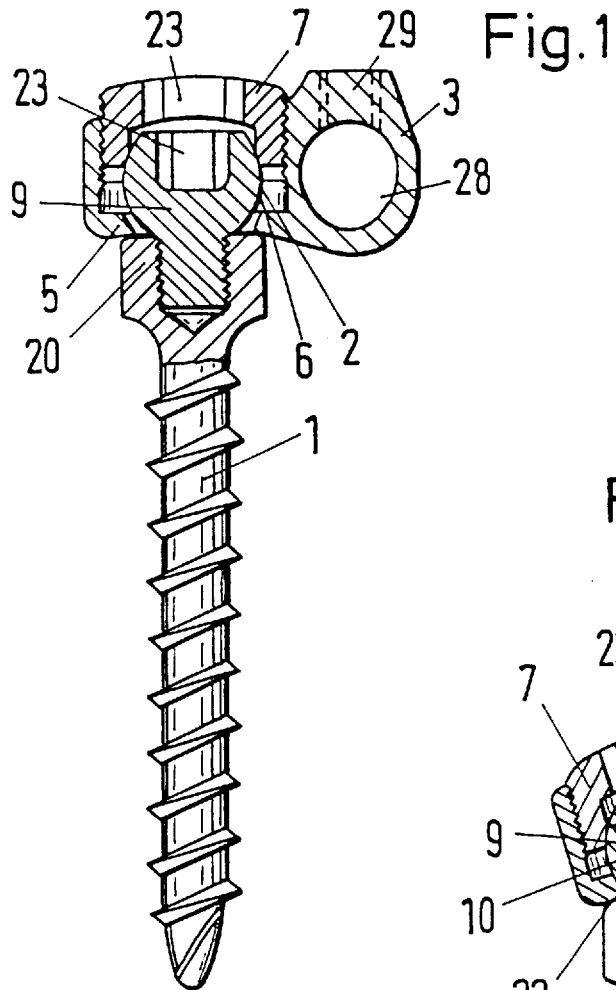
FIG. 1 is schematically, a pedicle screw with a separate spherical head part which is formed as a screw.

A pivotal securing system between a bone screw 1 comprising a spherical head part 2 and a reception part 3 is shown in the figures. The reception part has a passage bore 4 with a shoulder at its end which encloses the head part 2 at its lower side and which forms an abutment when the head part 2 is pressed on by the clamping screw 7 in a settable pivotal position 8. The head part 2 is executed as a separate part 9 which can be screwed together with the bone screw 1 in order to be able to place on the reception part 3 and to connect it to the latter after the implantation of the bone screw 1.

In FIGS. 1, 2, 3, 4, 5, 15 and 17 the same reception part 3 is shown repeatedly, which, as a securing system 17, receives a connection rod 18 in a bore 28 and is secured to it with one or two setscrews 24 which are sunk into threaded bores 29. A lug (FIG. 17) is formed on at the side with a passage bore 4 which is arranged transverse and displaced with respect to the bore 28 and has an inwardly projecting ring shaped shoulder 5 at its lower end. Above the shoulder 5 the passage bore 4 is broadened to such an extent that a spherical head part 9, 10 of a pedicle screw 1 is caught by the shoulder 5 and can be pressed onto the latter with a clamping screw 7. Since the pedicle screws 1 are equipped with a spherical head part 2 which can be screwed together with the pedicle screw 1 as a separate part 9, there are many more freedoms in the shaping of the individual pedicle screws without it being necessary to do without a pivotability about a spherical head.

In FIG. 1 the pedicle screw 1 is provided with a collar 20 which has an outer hexagon in order to turn in the screw 1. The collar 20 has a bore with an inner thread in order to receive the separate spherical head part 9 at an inner hexagon 23 and to screw it into this bore after the reception part 3 has been placed on. The spherical head part 9 is drawn tight against an abutment which is provided by a terminating thread or by the front surface of the collar 20. It is essential that the shoulder 5 is caught by the lower side 6 of the spherical head 2 with sufficient clearance so that the provided pivotal range can be moved through when the shoulder 5 is placed in contact with the spherical head 2. The clamping screw 7 is executed as a cover screw with an inner hexagon 23. Instead of the inner hexagon 23 two blind holes displaced away from the axis could also serve as application surfaces for turning on the cover screw 7 and provide approximately closed spaces between the cover screw 7 and the shoulder 5.

Figure 2:
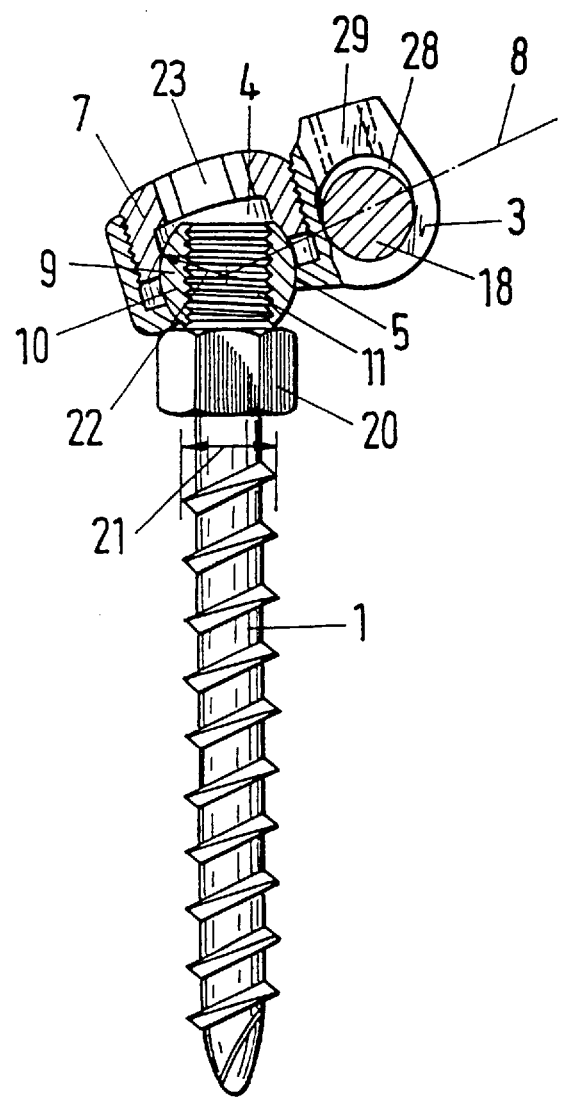
FIG. 2 is schematically, a pedicle screw with a separate spherical head part which is formed as a nut.
Figure 17:
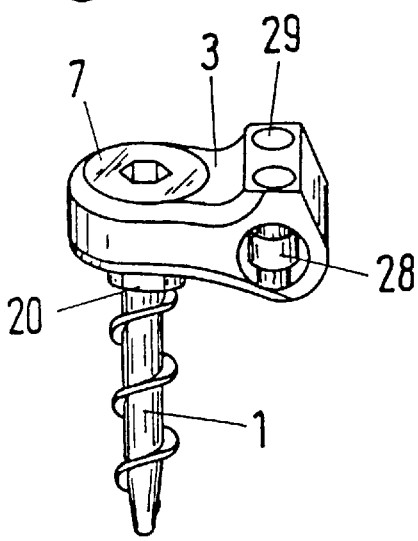
FIG. 17 is schematically, on a smaller scale, a view of a reception part which is connected to a bone screw.

In FIG. 2 a similar reception part 3 is secured with a similar cover screw 7 in a pivotal position 8 to a separate spherical head part 9 which is designed as a screw nut 10 which is firmly screwed to a screw shaped extension 11 of the pedicle screw 1 and lies in contact against its collar 20. The thread of the actual pedicle screw 1 has a diameter 21 which may well be greater than the inner diameter 19 (FIG. 5) of the shoulder 5. The spherical radius 22 of the screw nut 10 stands in a definite relationship to the diameters of the pressing surfaces of the shoulder 5 and the clamping screw 7, which is given by the cone angles of average conical pressing surfaces, as will be shown later.

Figure 3:
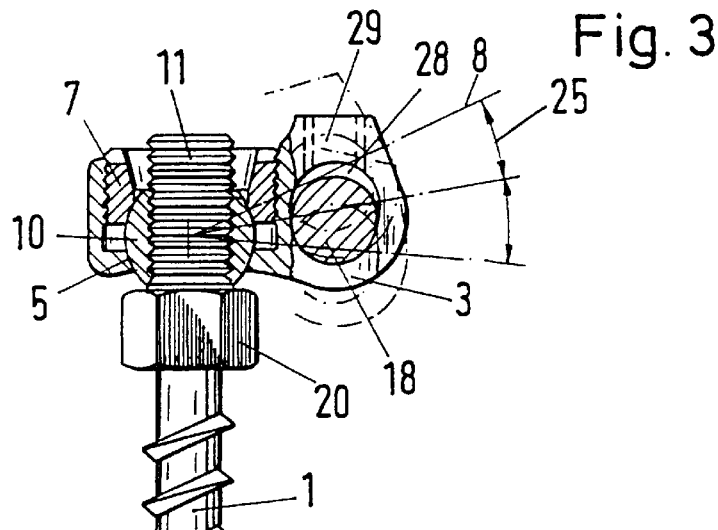
FIG. 3 is schematically, a standard pedicle screw with a separate spherical head part which is formed as a nut and with a pivotal reception part.
Figure 4:
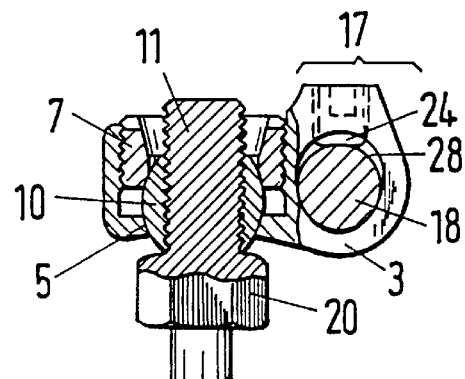
FIG. 4 is schematically, an arrangement in accordance with FIG. 3 with a fixed connection rod.
Figure 15:
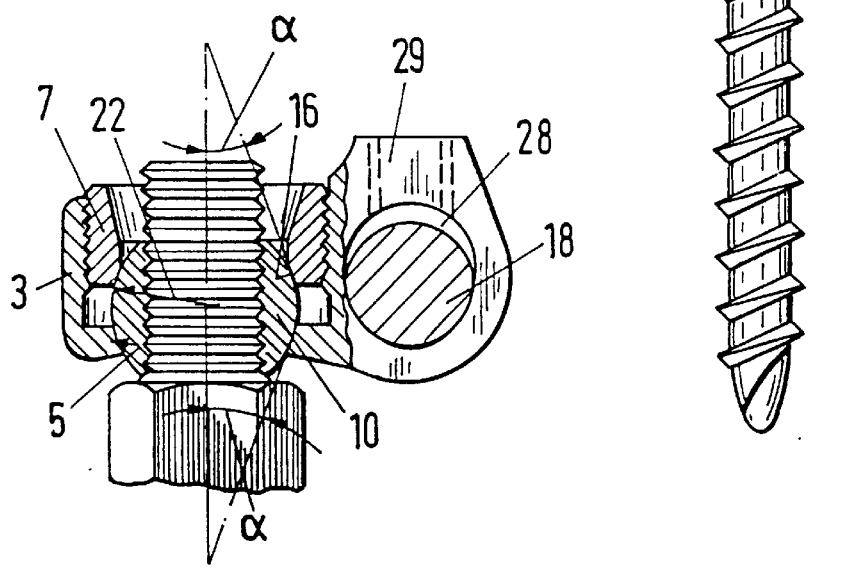
FIG. 15 is schematically, an enlarged section of FIG. 3, in which the half cone angle at the reception part and the clamping screw can be seen.
Figure 7:
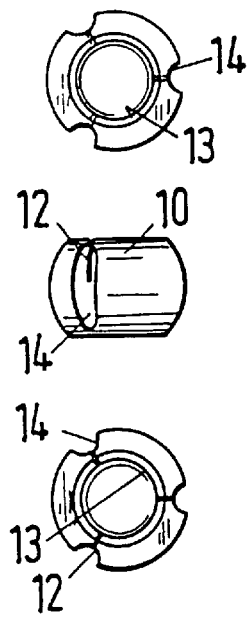
FIGS. 7 to 14 are schematically, in each case a side view of a spherical screw nut which is provided with a slit and an engagement surface and their projections in the direction of the screw axis.
Figure 8:
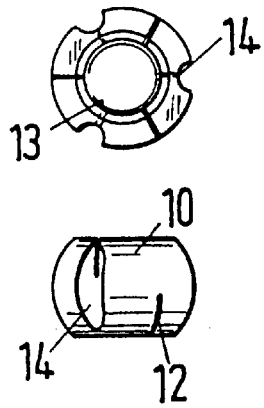
Figure 9:
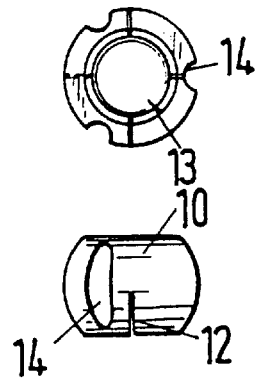
Figure 10:
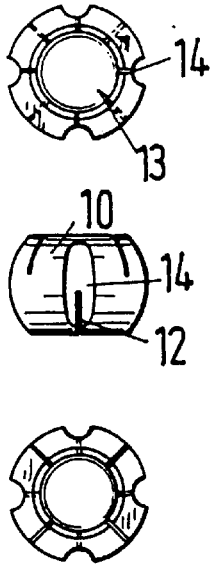

FIGS. 3, 4 and 15 show a standard pedicle screw 1 with a relatively long screw-shaped extension 11. In FIG. 3 the clamping screw 7 is turned in only slightly and permits deviations 25 of the pivotal position 8 from a central pivotal position which can be on the order of magnitude of plus or minus 15° if, as can be seen in FIG. 15, the pressing surface of the support shoulder 5 and the pressing surface 16 of the clamping screw 7 are conical surfaces with a half cone angle $8°<\alpha<25°$. The conical pressing surfaces have the advantage that the force application points at the spherical head 10 are preserved if the latter deforms inwardly as a result of an intentional weakening. A half cone angle $\alpha \approx 20°$ is seen as advantageous for this case. Since the screw-shaped extension 11 of the illustrated pedicle screw 1 is made longer than the height of the spherical head 10, a conical bore is placed in the clamping screw 11 which allows the maximum provided pivoting. The clamping screw 10 is provided with cut-outs on its upper side which permit the placement of a screwing-in tool. In FIG. 4 the clamping screw 7 is fixed on the spherical screw nut 10. As long as the screw nut 10 does not deform inwardly to such an extent that the thread clearance between the screw nut 10 and the screw-shaped extension 11 is cancelled, only the frictional forces which are produced by the tightening of the screw nut 10 on the collar and the thread are responsible for the torque which can be transmitted to the pedicle screw with respect to the screw axis of the reception part 3.

Figure 11:
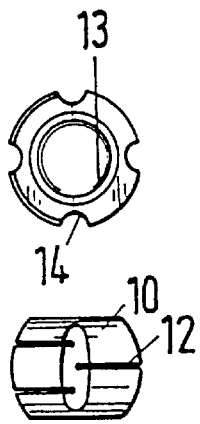
Figure 12:
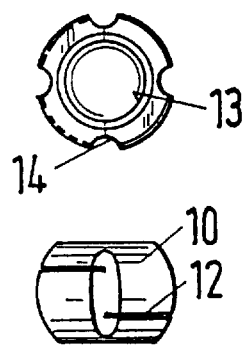
Figure 13:
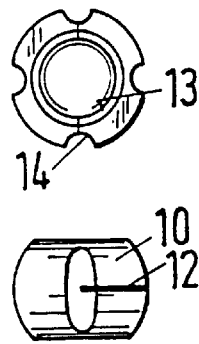
Figure 14:
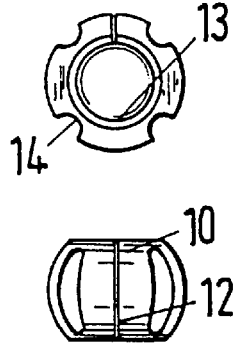

The FIGS. 7 to 14 thus show a variety of artificially weakened spherical screw nuts 10 which in this case are weakened by additional slits 12 which pass through the thread in order to achieve an inward deformation of the thread passages and an additional cramping on the screw-shaped extension 11 when being pressed together between the conical pressing surfaces 16, 5. In FIGS. 7, 8, 9, 10, 14 the slits lie in planes which pass through the axis of the pedicle screw. In FIGS. 11, 12, 13 the slits lie in planes which are perpendicular to the axis of the pedicle screw. Other weakenings through incisions and notches are likewise conceivable if they lead to a reduction of the thread diameter 13 at the spherical screw nuts 10. At the outer side of the screw nuts 10, engagement surfaces 14 in the form of cylindrical cut-outs are provided which permit the turning in with a screw tool 15 (FIG. 16) which has suitable projections 26.

FIG. 5 shows an anchoring of the screw nut 10 without an abutment. The turning in of the pedicle screw is done at the upper end at an inner hexagon 23. After the pedicle screw 1, of which the thread diameter 21 may likewise be greater than the inner diameter 19 of the shoulder 5, has been turned in, the reception part 3 can be placed on. Then the spherical screw nut 10 is screwed in at a suitable height at the screw-shaped extension 11. Then the clamping screw 7 is screwed in and the reception part 3 is pivoted into a suitable direction. When the clamping screw 7 is turned tight with respect to the reception part 3 the deformable spherical nut 10 seats itself firmly on the thread and is blocked. With the help of the conical pressing surfaces 16, 5 and the number and size of the cut-outs 14, local plastic deformations can be intentionally produced which produce a rigid connection between the screw nut 10 and the pressing surfaces 16, 5.

In order to emphasise the modular nature of the invention, FIG. 6 shows how the standard pedicle screw 1 and the reception part 3 of FIG. 3 can also be directly mutually adjustably fixed in a plane with respect to the angle of rotation with a securing nut 27. The clamping of the shoulder 5 takes place between the collar 20 and the securing nut 27.

The nut 10 in FIGS. 18 and 19 is provided with slits 12 only up to two thirds of the way from above so that a connected threaded part arises in the lower part for the inner thread 13. A neck 30 is additionally formed on which projects outwardly at an inclination and is supported on a shoulder of the bone screw 1. Using a non-illustrated turning-in tool, the nut 10 can be grasped at engagement surfaces 14 and screwed towards the shoulder 20 against a bias force. A bending torque acting at the spherical surface of the nut primarily effects an increase of the compression stresses in the neck 30 and an increase of the tension stresses in the screw-like extension 11 of the bone screw 1. In contrast to a pure bending stress with a neutral phase and with tension and compression stresses increasing in the outward direction, the screw-like extension 11 is tension stressed over its entire cross-section, with substantially lower tension peaks arising.

In FIGS. 20, 21 and 22 a general improvement of clamping screws 7 for spherical heads is shown. The pressing surface 16 is the section of an inner cone which was provided with a multiple thread 31, 31a in the form of spiral grooves, with a groove 31a being directed the same as the outer thread 32 of the clamping screw 7 and having a pitch 33 like that of the outer thread in order to achieve a greater mutual penetration of the spherical surface and the multiple thread. For the transmission of a large drawing-in torque, four cross-wise arranged grooves 34 are provided in the upper region of the clamping screw.

What is claimed is:

1. A securing system between a bone screw having a spherical head part and a reception part which at the end of a passage bore encloses the head part with a shoulder at its lower side and which receives a clamping screw in the passage bore by means of which the head part can be pressed on against the shoulder in a selectable pivotal position, the spherical head part being a separate screw nut which can be screwed together with a threaded extension of the bone screw.

2. The securing system in accordance with claim 1 wherein the screw nut is weakened towards the outside by at least one slit of an inner thread in order to fix the inner thread during the pressing together of the spherical screw nut through a deformation of thread paths on a threaded extension.

3. The securing system in accordance with claim 1 whereby the spherical screw nut has engagement surfaces which enable the placing on of a screw tool.

4. The securing system in accordance with claim 1 where the shoulder and a press-on surface of the clamping screw each include a conical surface.

5. The securing system in accordance with claim 4 where each conical surfaces has a half cone angle between 8° and 25°.

6. The securing system in accordance with claim 5 where each conical surface has a half cone angle $\alpha \approx 20°$.

7. The securing system in accordance with claim 1 where the reception part has a further mounting for a connection rod.

8. The securing system in accordance with claim 1 where the bone screw has a collar which projects outwardly over an inner diameter of the shoulder.

9. The securing system in accordance with claim 1 where a thread diameter of the bone screw is greater than and inner diameter of the shoulder.

10. The securing system in accordance with claim 1 where a the screw nut has a neck which forms a closed ring and which is supported outside an outer diameter of the thread extension on a shoulder of the bone screw.

11. The securing system in accordance with claim 2 where a press-on surface of the clamping screw is provided with an inner thread which is directed the same as an outer thread of the clamping screw and has a similar pitch in order that the inner thread forms in a groove when the clamping screw is drawn on to the spherical head part which improves the torque which can be transmitted to the spherical head part.

12. The securing system in accordance with claim 11 where the inner thread forms a plurality of grooves in order to increase the number of thread peaks acting on the spherical head part.

13. A pivotal securing system between a bone screw having a spherical head part and a reception part which at the end of a passage bore encloses the head part with a shoulder at its lower side and which receives a clamping screw in the passage bore by means of which the head part can be pressed on against the shoulder in a selectable pivotal position, where the spherical head part is executed as a separate part which can be screwed together with the bone screw in order to be able to place on the reception part and to connect it to the bone screw after the implantation of the bone screw and where a press-on surface of the clamping screw is provided with an inner thread which is directed the same as an outer thread of the clamping screw and has a similar pitch in order that the inner thread forms in a groove when the clamping screw is drawn on to the spherical head part which improves the torque which can be transmitted to the spherical head part.

* * * * *